(12) United States Patent
Young Anze et al.

(10) Patent No.: US 9,259,445 B2
(45) Date of Patent: Feb. 16, 2016

(54) INTEGRATED IMPLANT SYSTEM (IIS) BIOCOMPATIBLE, BIODEGRADABLE AND BIOACTIVE, COMPRISING A BIOCOMPATIBLE STERILE POROUS POLYMERIC MATRIX AND A GEL, INTEGRATING IN SITU THE TRIDIMENSIONAL MATRIX STRUCTURE

(75) Inventors: Manuel Eduardo Young Anze, Valparaiso (CL); Cristian Andrés Acevedo Gutiérrez, Valparaiso (CL); Fernando Antonio Albornoz Marquez, Valparaiso (CL); Caroline Ruth Weinstein Oppenheimer, Valparaiso (CL); Alexis Roobins Aceituno Alvarez, Valparaiso (CL); Donald Irving Brown Gonzalez, Valparaiso (CL); Sergio Miguel Tapia Murua, Valparaiso (CL)

(73) Assignees: UNIVERSIDAD TECNICA FEDERICO SANTA MARIA, Valparaiso, V Region (CL); UNIVERSIDAD DE VALPARAISO, Valparaiso, V Region (CL); FUNDACION INSTITUTO DE SEGURIDAD DEL TRABAJO, Valparaiso, V Region (CL)

( * ) Notice: Subject to any disclaimer, the term of this patent is extended or adjusted under 35 U.S.C. 154(b) by 1250 days.

(21) Appl. No.: 12/303,714

(22) PCT Filed: Jun. 7, 2007

(86) PCT No.: PCT/EP2007/005060
§ 371 (c)(1),
(2), (4) Date: Jun. 11, 2010

(87) PCT Pub. No.: WO2007/141028
PCT Pub. Date: Dec. 13, 2007

(65) Prior Publication Data
US 2010/0255052 A1    Oct. 7, 2010

(30) Foreign Application Priority Data
Jun. 7, 2006    (CL) .................................. 1397-2006

(51) Int. Cl.
*A61F 2/10*    (2006.01)
*A61K 35/36*    (2015.01)
*C12N 5/00*    (2006.01)

(52) U.S. Cl.
CPC .............. *A61K 35/36* (2013.01); *C12N 5/0012* (2013.01); *A61F 2/105* (2013.01); *C12N 2533/56* (2013.01)

(58) Field of Classification Search
None
See application file for complete search history.

(56) References Cited

U.S. PATENT DOCUMENTS

| | | |
|---|---|---|
| 6,733,530 B1 | 5/2004 | Lam et al. |
| 2003/0095993 A1 | 5/2003 | Bentz et al. |
| 2003/0170892 A1 | 9/2003 | Boyce |
| 2005/0261736 A1* | 11/2005 | Murray et al. ................ 606/214 |
| 2009/0214614 A1* | 8/2009 | Everland et al. ............. 424/423 |

FOREIGN PATENT DOCUMENTS

| | | |
|---|---|---|
| CA | 2497895 | 3/2004 |
| CL | 1397/2006 | 7/2007 |
| CN | 1468634 A | 1/2004 |
| CN | 1562392 A | 1/2005 |
| FR | 2657352 A1 | 7/1991 |
| WO | WO 98/22154 A2 | 5/1998 |
| WO | WO 98/40111 A1 | 9/1998 |
| WO | WO 02/078721 A1 | 10/2002 |
| WO | WO 2007/141028 A2 | 12/2007 |

OTHER PUBLICATIONS

"Micropatterning of proteins and mammalian cells on biomaterials," Wang, Y. and Ho, C-C, The FASEB Journal, express article 10.1096/fj.03-0490fje, published on-line Jan. 8, 2004.*
Liu, H., et al., "A study on a chitosan-gelatin-hyaluronic acid scaffold as artificial skin in vitro and its tissue engineering applications," J. Biomater. Sci. Polymer Edn, 2004, vol. 15, No. 1: pp. 25-40.
Alvarez-Diaz, C. et al., "Controlled Clinical Study of Deep Partial-Thickness Burns Treated With Frozen Cultured Human Allogeneic Epidermal Sheets," Journal of Burn Care & Rehabilitation, Jul./Aug. 2000, vol. 21, No. 4: pp. 291-299 (9 pages).
Bello, Y.M. et al., "Tissue-Engineered Skin: Current Status in Wound Healing," Am J Clin Dermatol, 2001, vol. 2, No. 5: pp. 305-313 (9 pages).
Betterman, A. et al., "Cultivation of human skin cells in fibrin microcapsules," Second International Congress—Current Concepts in Pediatric Burn Care, Oct. 13-16, 1999, Florence, Italy, conference information with pp. 147-152 (8 pages).
Carsin, H. et al., "Cultured epithelial autografts in extensive burn coverage of severely traumatized patients: a five year single-center experience with 30 patients," Burns, 2000, vol. 26: pp. 379-387 (9 pages).
Cox, S. et al., "Behavior of Human Dermal Fibroblasts in Three-Dimensional Fibrin Clots: Dependence on Fibrinogen and Thrombin Concentration," Tissue Engineering, 2004, vol. 10, No. 5/6: pp. 942-954 (13 pages).
Curran, M.P. et al., "Bilayered Bioengineered Skin Substitute (Apligraf® 1): A Review of its Use in the Treatment of Venous Leg Ulcers and Diabetic Foot Ulcers," Biodrugs, 2002, vol. 16, No. 6: pp. 439-455 (17 pages).

(Continued)

*Primary Examiner* — David J Blanchard
*Assistant Examiner* — Daniel F Coughlin
(74) *Attorney, Agent, or Firm* — Hasse & Nesbitt LLC; Daniel F. Nesbitt

(57) ABSTRACT

The present invention refers to an Integrated Implant System constituted as a gel-matrix-cells integrated system, that allows providing implants in a brief time period, for covering a great skin extension to be treated, with a successful acceptance in patients with burns, chronic damage or wound skin, needing of a skin grafting.

7 Claims, 2 Drawing Sheets

(56) References Cited

OTHER PUBLICATIONS

Deblois, C. et al., "Heparin-fibroblast growth factor-fibrin complex: in vitro and in vivo applications to collagen-based materials," Biomaterials, Jul. 1994, vol. 15, No. 9: pp. 665-672 (8 pages).

Doillon, C.J. et al., "Bioactive collagen sponge as connective tissue substitute," Materials Science and Engineering, Dec. 1, 1994, vol. C2: pp. 43-49 (7 pages).

Eisenbud, D. et al., "Skin Substitutes and Wound Healing: Current Status and Challenges," Wounds, Jan. 2004, vol. 16, No. 1: pp. 2-17 (16 pages).

Hansbrough, J.F. et al., "Clinical Trials of a Biosynthetic Temporary Skin Replacement, Dermagraft-Transitional Covering, Compared with Cryopreserved Human Cadaver Skin for Temporary Coverage of Excised Burn Wounds," Journal of Burn Care & Rehabilitation, Jan./Feb. 1997, vol. 18, No. 1, Part 1: pp. 43-51 (9 pages).

Khachemoune, A. et al., "Factors that Influence Healing in Chronic Venous Ulcers Treated with Cryopreserved Human Epidermal Cultures," Dermatol Surg, Mar. 2002, vol. 28, No. 3.: pp. 274-280 (7 pages).

Lam, P.K., et al., "Development and Evaluation of a New Composite Laserskin Graft," Journal of Trauma: Injury, Infection and Critical Care, Nov. 1999, vol. 47, No. 5: p. 918 (13 pages).

Liu, H., et al., "A study on a chitosan-gelatin-hyaluronic acid scaffold as artificial skin in vitro and its tissue engineering applications," J. Biomater Sci Polym Ed., 2004, vol. 15, No. 1: pp. 25-40. (missing pp. 28 & 38).

Maas-Szabowski, N. et al., "Keratinocyte Growth Regulation in Defined Organotypic Cultures Through IL-1 Induced Keratinocyte Growth Factor Expression in Resting Fibroblasts," J Invest Dermatol, 2000, vol. 14: pp. 1075-1084 (10 pages).

Michel, M. et al., "From Newborn to Adult: Phenotypic and Functional Properties of Skin Equivalent and Human Skin as a Function of Donor Age," J Cell Physiol, 1997: vol. 171: pp. 179-189 (11 pages).

Naughton, G. et al., "A Metabolically Active Human Dermal Replacement for the Treatment of Diabetic Foot Ulcers," Artificial Organs, 1997, vol. 21, No. 11: pp. 1203-1210 (8 pages).

Pollak, R.A. et al., "A Human Dermal Replacement for the Treatment of Diabetic Foot Ulcers," Wounds, Nov./Dec. 1997, vol. 9, No. 6,: pp. 175-183 (9 pages).

Stark, H.-J. et al., "Organotypic Keratinocyte-Fibroblast Cocultures: In Vitro Skin Equivalents to Study the Molecular Mechanisms of Cutaneous Regeneration." In: *Cultured Human Keratinocytes and Tissue Engineered Skin Substitutes*, by Horch RE, Munster AM, Achauer BM (eds), Stuttgart, Germany: Georg Thieme Verlag, 2001, pp. 163-172 (10 pages).

Tay, A.G., et al., "Cultured Subconfluent Keratinocytes on Wound Polymer Dressings in the Treatment of Burns and Chronic Wounds," vol. 12, No. 5: pp. 123-129 (9 pages), 2000.

\* cited by examiner

| Rabbit | Cell/cm² | % keratinocyte | % Fibroblastes |
|--------|----------|----------------|----------------|
| C2  | 6,8 x 10⁴ | 67 | 33 |
| C4  | 1,6 x 10⁴ | 43 | 57 |
| C5  | 1,9 x 10⁴ | Natural Coculture | |
| C6  | 4,0 x 10⁴ | 67 | 33 |
| C7  | 3,8 x 10⁴ | 8  | 92 |
| C9  | 1,4 x 10⁴ | 30 | 70 |
| C11 | 1,6 x 10⁴ | 63 | 37 |
| C13 | 1,5 x 10⁴ | 31 | 69 |
| C14 | 2,9 x 10⁴ | 9  | 5  |

INTEGRATED IMPLANT SYSTEM (IIS) BIOCOMPATIBLE, BIODEGRADABLE AND BIOACTIVE, COMPRISING A BIOCOMPATIBLE STERILE POROUS POLYMERIC MATRIX AND A GEL, INTEGRATING IN SITU THE TRIDIMENSIONAL MATRIX STRUCTURE

CROSS REFERENCE TO RELATED APPLICATIONS

This is the National Stage of International Application PCT/EP2007/005060, with an international filing date of Jun. 7, 2007, which claimed the benefit of Chilean Patent Application No. 1397/2006, filed Jun. 7, 2006.

FIELD OF THE INVENTION

The present invention is related to an Integrated Implant System easy to use and handle for being applied in surgical grafting. It is constituted as a gel-matrix-cells integrated system, a feature that allows providing implants in a brief time period, for covering a great skin extension to be treated, with a successful acceptance in patients with burns, chronic damage or wound skin, needing of a skin grafting.

BACKGROUND OF THE INVENTION

Skin is the largest organ of the body, covering the body's outer surface area. Skin is composed of two main layers: the surface epithelia or epidermis, containing epidermal cells as keratinocytes, and the underlying connective tissue layer or dermis, containing dermal cells as fibroblasts. Several and important functions are associated to the skin, for instance, the protection against injury and dehydration, acting as a barrier against infections, perceiving or detecting environmental stimuli, excreting diverse substances, regulating the body temperature, and helping to maintain the hydric balance. Substantially intact and healthy skin is needed, not only for the body welfare, but for its survival.

The skin health and integrity may be affected by congenital or acquired pathological conditions, either acute or chronic, for which the natural skin repair and regeneration processes may be insufficient. These conditions include burns, wounds, ulcers, infections, congenital diseases and/or abnormalities. Therefore, a non-appropriate condition and state of the skin is extremely harmful, since it affects the health condition and the organism existence. Those patients that have been affected by burns in a vast surface area of their bodies often require an immediate and extensive replacement of skin. In addition, some less life threatening conditions can be present, however considered as chronic conditions of skin, for instance as occurs for passive hyperemia, the diabetic ulcers or decubitus ulcer, which may result in more severe conditions, if no treatment is applied, particularly since those patients exhibiting these conditions suffer an underlying pathology. On the other hand, the morbidity and mortality drop-off in this kind of patients depends of the appropriate and effective restoration of the skin structure and function.

Skin substitutes may be used for treating these or other conditions. The desirable properties for skin substitutes are availability and handling, low rejection degree, high adherence degree, highly independent from a skin donor, relative easiness for being produced from a skin biopsy of a minimal size, and the feature of a cost-effective production and use.

Several methods for elaborating skin substitutes have been assayed, which satisfy some or all these requirements, but with varied success degrees.

However, a predominant design for a skin substitute, which satisfactorily is able of regenerating all the skin structures and functions, is not available yet. Only, a full thickness skin graft is able to virtually restoring all the normal non damaged skin structures and functions. Large and extensive information is available about commercial devices or technical solutions for solving this skin graft problem, nevertheless these do not provide the qualities and advantages of the development described in the present invention.

US 2003/0170892, describes a device comprising a cell-free biocompatible reticulated matrix, wherein a first (layer) of dermal cells are cultured, and over these cells, epidermal cells are grown. Further, it describes the method for producing said device, useful for applications in skin wounds, in therapeutic treatment and/or for the in vitro assay of human skin. Providing similar structures and functions to a normal healthy skin, as a barrier function.

The above development exhibits clear differences and disadvantages regarding the present invention, since the described implant corresponds to a device comprising cells grown in the surface and in clearly differentiated layers. Furthermore, due to the design and the method for producing said device, the required time for applying the same is longer than 24 hours, considered from the moment when the dermal cells culture is available for being seeded over the matrix.

CN 1562392 describes a method for preparing an artificial skin in an active bi-layer supported on a collagen sponge, which is cultured in a bioreactor with a fibroblasts suspension for generating the dermis and on top of this, epidermal cells are seeded. Structural differences with the corresponding graft of the present invention, can be clearly distinguished since this document mentions a layer type of graft exhibiting cells on the surface, wherein the seeding method is less efficient, more complex, more expensive and takes longer time for reaching similar results. The same differences regarding the present invention are observed for the patent application CN 1468634, wherein an artificial skin implant with a double film is described, with superficial growth of epidermal cells over a fibroblasts-PGA structure.

U.S. Pat. No. 6,733,530 describes a device wherein autologous keratinocytes are grown over a biocompatible substrate, which is pre-seeded with allogenic or autologous dermal fibroblasts, which can be applied over an artificial skin substrate grafted to the receptor patient. The layered and superficial structure of the device, and the method for preparing the same, described in this document, makes the present invention a different device with clear advantages regarding the applications of the same.

In a same way to the preceding cases, in the patent CA 2497895 is described a fibrin cell support to form cell cultures. It is possible to establish cell cultures on this support, such as keratinocytes cultures. In a disclosed embodiment, it is possible to incorporate cells in the fibrin gel structure. The above description considerably differs from the present invention device, since the present invention corresponds to a gel-matrix-cells integrated device, which exhibits better handling characteristics as it comprises a biocompatible support available as the porous matrix, which contributes to device strength, resistance and flexibility. In fact, the presence of a biocompatible support does not form part of what is described in the document, since the fibrin gel is used in combination with a preliminary treatment of the wound with artificial skin (Integra™). Furthermore, in the document the product is applied as a paste or spray on the wound, which implies great difficulties for fixing the fibrin gel to the wound and for being properly accepted by the grafted patient. Accordingly, combined additional or supplementary treatments are needed, in order to allow the graft fixing to the wound, since the fibrin gel slides from the application site. In the present invention no fixing or additional treatments are required in order to maintain the device on the application site and to start the regeneration of the damaged skin. Although in the reference is mentioned the incorporation of polymers, these function only as fibrin carriers, furthermore these are not incorporated into the fibrin gel, as in the present invention. The above provides a different support with a closer in situ integration of the matrix-gel, corresponding to one of the present invention contributions.

In the same way the patent application WO02078721 describes a system for providing an autologous in situ implant, wherein a keratinocytes and fibroblasts suspension containing fibrin, are mixed with a thrombin, fibrinogen and collagenase solution. As in the latter case, the reference differs from the present invention, as it is not related to an integrated device comprising a biocompatible support as a porous matrix. At the same time, in the present invention the strength, handling and adherence properties are improved and optimized, regarding the technical solution disclosed in the document WO02078721. Furthermore, the physical qualities of strength and the in situ preparation, makes this product difficult to handle and store, since it corresponds to a cell suspension which is applied in the site to be treated (wound or damaged tissue), exhibiting adherence difficulties such as described for the previous document.

The main purpose of the skin substitutes is to save the patient's life, providing a coating or barrier, which prevents the skin dehydration and infection. A second objective is to allow for a functional healing, which additionally should be cosmetically acceptable.

Different cell types and material combinations, which have been evaluated for producing cutaneous substitutes, are nowadays commercially available. Most of said commercial products are formed by allogenic cells-containing matrix, generally from neonatal foreskin, which exhibits the advantage of containing a higher number of stem cells for keratinocytes, potential mitogenic properties, an exacerbated metabolism and minimal antigenicity[1,2].

One of the known most simple cutaneous substitutes is EPICEL®, which is composed by autologous keratinocytes arranged on a paraffined gauze, which is a non biodegradable material. Said cells are obtained from a full thickness biopsy from the injured subject, the cells are subsequently grown over a layer of murine fibroblasts, which have previously been irradiated. Thus, stratified keratinocytes layers are achieved, containing from two to eight layers[3]. In this system, rejection is totally avoided and the cells are permanently incorporated into the tissue. However, it is fragile and with poor cosmetic ability of maintaining an acceptable appearance in the patients. Some available studies indicate that implanting stratified keratinocytes (differentiated) is not the most suitable approach, since the higher differentiating degree and the lower proliferating ability. It is preferable, such as is provided by the present invention, to implant cells with the least number of in vitro passages.

A retrospective study carried out in a 30 patients group, exhibiting burns that cover 78% of the body surface, treated with EPICEL®, an extremely high survival rate (90%) was informed[4]. Nevertheless, the higher difficulty of this treatment is related to its cost and logistics.

Other known product, based in autologous cells is Laserskin®, which is indicated for the treatment of second-degree deep burns and for chronic ulcer. This product consists of a biodegradable estherified hyaluronic acid matrix, with laser made micro-perforations in order to allow the keratinocytes settlement and proliferation. Said autologous keratinocytes are obtained from a biopsy and are directly cultured in the mentioned matrix. Laserskin®, is only available in Europe. The efficiency in treating the diabetic foot ulcer has been demonstrated for this product; however no controlled clinical trials are available. This device can be used combined with Hyaff™ a support containing dermis fibroblasts, wherein the fibroblasts can be autologous or allogenic. These products correspond to devices wherein cells can be grown within their matrix, not only in the surface, nevertheless, these do not correspond to an in situ integrated system formed by matrix-gel cells as the one of the present invention.

On the other hand, Celaderm® is a commercially available product, this product contains metabolically active foreskin-derived heterologous keratinocytes which however are unable of proliferating. This product has been used for treating chronic ulcer; and as a further advantage, it can be cryo-preserved[6]. Some available studies reveal the effectiveness of this product in burns, however not compared with autografting[7]. This product exhibits significant differences regarding the present invention, as it does not involve an integrated system.

Other known product is Dermagraft®, an approved substitute for treating diabetic foot ulcer. In this case, fibroblasts are obtained from neonatal foreskin and cultured on a polyglactine matrix, during approximately three weeks. In this term, cells secrete matrix proteins, providing a tridimensional in situ matrix which serves as a dermis substitute. The product is delivered cryo-preserved and requires thawing and washing to be used[8].

Other product is Transcytee® (originally known as Dermagraft-TC®) containing non-viable fibroblasts on a silicone-covered nylon net. Said product is prescribed as a temporary cover or coating for burn wounds which have been split by surgery, as an alternative for cadaver skin[9,10].

Other allogenic product is the one known as LSE, primary used in the treatment of the diabetic foot and the venous leg ulcers[11]. The LSE corresponds to a cutaneous substitute composed by a collagen matrix with viable fibroblasts and a stratified epidermal layer. One difference regarding the present invention is that it corresponds to an integrated device without forming stratified or differentiated epithelia.

The OrCel® product is very similar to the previous one with the difference that the dermal matrix is a porous, crosslinked type II collagen sponge, instead of a gel. The sponge is non symmetrical, in a way that a side is covered by a layer of an acid soluble atelocollagen gel, for sealing the macroscopic pores. Fibroblasts are grown on or within the porous side of the collagen sponge, while the keratinocytes are cultured in the non-porous side, covered by the gel of this collagen matrix. The cells seeded matrix is kept submerged for inhibiting differentiation and stratification of keratinocytes. The time and ratio for the fibroblasts and keratinocytes seeding are designed for controlling the cellular density and the cytokines expression in the final product. It has been seen that the co-culture of fibroblasts and keratinocytes exhibits synergic effects over the production levels of some cytokines and growth factors[12-13].

The PolyActive™ product, uses polyethylene oxide/polybutylphtalate (PEO/PBT) and may use the own patient fibroblasts for the dermis, and the own patient keratinocytes cultured for the epidermis. Finally, Integra™ which uses a collagen-glycosaminoglycan matrix (GAG) providing a non cellular or acellular dermal component, and which may use a thin autograft or other devices containing cells.

The tissue engineering discipline, intended to the generation of a solution for burned patients, or with disability scars or cutaneous ulcers, is an area of great scientific interest. Numerous scientific publications can be found, wherein products are described, which contain autologous or heterologous cells, in combination with some different nature matrix.

In general, the market known and existing products exhibit differences and disadvantages regarding the present invention. The main differences are that said devices do not correspond to an in situ integrated device with a fibrin gel and a biocompatible polymer. Among the disadvantages of the state of the art devices, the content of bovine nature components can be found; therefore, it should be considered that these products soon will no longer be used, due to the appearance of prion contamination cases in USA, the need of long incubating or preparation periods, and the differentiation degree (stratification) for the cells, as keratinocytes, which are non favorable factors for these devices.

In the literature, there are many studies carried out in animals, which show that the presence of cells in an implant is beneficial for the healing of a cutaneous injury and that this benefit is higher if the cells are autologous. Most of the commercial products use heterologous fibroblasts from neonatal foreskin. The selection of this type of cells is due to the easiness for growing them in vitro. However, these cells are heterologous, what additionally implies a rejection risk, the needing of carrying out expensive analysis for guarantying that they are not contaminated with microorganisms, such as HIV or with C hepatitis virus, among others. Additionally, the products comprising only fibroblasts, may influence on a non desirable healing, from an aesthetic point of view as for the fibroblasts may be differentiated into myofibroblasts, responsible of the non desirable contraction of the wound.

Besides products are known wherein autologous dermal and epidermal cells are used. Nevertheless, these are products that distribute the cells in different layers, on a same support, in different faces of the support or in different supports. Generally, said products, are difficult of handling and the availability timing for applying the device is of more than 24 hours, since it is necessary to seed, attach and culture the cells over the surface of the supports or over the cultured dermal cells.

A clear disadvantage of the devices for grafting is the need of adhesives for fixing the implants onto the injuries. Mechanical devices or organic polymers can be used as attachers (stapples or gauze), wherein the main objective of these is to achieve the graft take, being this understood as the fixing of the device to the damaged skin, achieving the placement in the site to be treated.

Lyophilized pigskin has been used to immediate treatment of patients after the occurrence of a traumatic event. This is a transitory solution, since it only allows extending the patient life, while it is possible to apply definitive solutions. In addition, solutions have been developed, on the base of materials that help for burns healing. However, they are cell-free solutions, which unlikely can be compared with the complexity and with the contribution and efficiency in the wound healing, which implies an integrated system with cellular components and a biocompatible matrix developed as part of the present invention.

Therefore, the present invention provides an integrated implant system, being this understood as an intimate link among cells-gel-support, wherein can be combined more than one type of dermal or epidermal, autologous, allogenic, xenogenic or chimeric cells, exhibiting favourable: handling characteristics, time for obtaining the same, application availability, adherence, almost no rejection by the patient, better cellular development and easy conservation. Further, it is informed an easy and fast process for obtaining these integrated implants, wherein the cells are incorporated in the support matrix, providing a device for immediately being applied or conserved.

DETAILED DESCRIPTION OF THE INVENTION

Figures 1, 2:
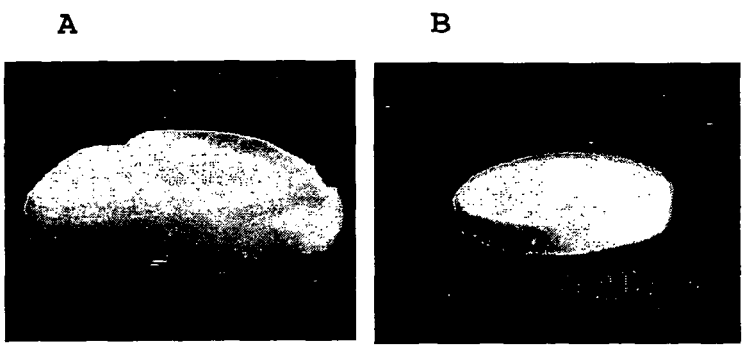
FIG. 1 shows a photography of the biocompatible cell free, microporous matrix, which is used in the present invention as the support for the integrated implant. Photograph A corresponds to the polymerized matrix and photograph B corresponds to the cross-linked matrix.
FIG. 2 corresponds to a table wherein different assays are identified, which are carried out in rabbits (column 1). The animal was surgically prepared, and then the integrated implant of the present invention was applied with different amounts of cells per implant area unit (column 2). In each case the ratio between keratinocytes (column 3) and fibroblasts (column 4) that are seeded in the implant varies, with the purpose of observing the differences in the wounds response as function of different proportions of skin cells of the implant.

The present invention corresponds to an integrated implant system (IIS), wherein into a matrix or porous support a gel or polymer components is incorporated and get absorbed into the matrix and in situ clots.

In a preferred modality, the present invention corresponds to an integrated implant system (IIS), wherein into a matrix or porous support are incorporated the components of a gel or polymer with an active agent or with the desired cells, which are absorbed in the inner part of the matrix, coagulating in situ. Wherein the active agent can be selected from the group consisting of: plants, animals or microorganisms natural extracts; chemicals, pharmaceuticals, cosmetics or polymers, their salts or derivatives; macromolecules or microorganisms.

IIS applications may be many and multiple, depending on the presence of active agents and/or cells. In the case it contains cells, the applications will depend of the features and the cell type to be applied in the IIS, the type of porous matrix and the polymer type to be integrated. Even, the SII could be used as a carrier, for therapeutic evaluation, for safety or efficiency of natural, chemical, pharmaceutical, cosmetic products, polymers or macromolecules. Nevertheless, in a preferred modality the application will be related to treating, curing, or delivering a benefit for pathologies o for chronic or acute injuries, affecting the skin of a mammal, preferably humans. Additionally, the invention comprises a method for preparing the IIS from isolated cells, which will be integrated into the matrix forming the gel-matrix-cells IIS.

In a preferred modality, the applications will be intended to problems related with burns, wounds, ulcers, infections, surgeries, diseases and/or congenital abnormalities of the skin. Particularly, the main objective and application of the invention is to be used as a surgical skin implant for burned people, chronic diseases or for regenerative treatments. Also the IIS can be used on a non damaged surface, a minimally damaged surface, or a surface that has surgically been prepared, and which for other reasons requires an IIS graft.

The IIS is composed by a biocompatible cell-free reticulated matrix, known as support or scaffold, providing an easy to handle support. Said scaffold may be acquired from those commercially available or may be prepared according to a production protocol, as is described below in the present invention or by other production protocol for preparing biocompatible polymers.

For preparing the IIS, it is possible to use a matrix composed of a full length natural or synthetic protein, or a polypeptide, as well as inorganic or organic polymers or their mixture. For example, a lyophilized collagen sponge can be used, either alone or combined with a carbohydrate (a mucopolysaccharide, such as a glycosaminoglycan (GAG), particularly chondroitin-6-sulphate). The collagen can be bovine tissue collagen, from bovine tendon, or from other bovine sources (bone or muscle), other xenogenic sources (for example from swine, sheep, goat, etcetera), of human origin, recombinant or a combination of any of the previous. Other proteins such as elastin or reticulin, or natural or synthetic amino acid polymers, may also be used.

One preferred embodiment for the matrix used in the present invention is composed by gelatin-chitosan-hyaluronic acid. Particularly, the matrix can be commercially available or it can be obtained according to the following process. In a preferred modality a matrix containing a concentration between about 0.5 to 5%, preferably between about 1 to about 3% of gelatin is used, a concentration between about 0.5 to 3%, preferably between about 1 to about 2% of chitosan is used, and a concentration between about 0.5 to 2%, preferably between about 0.8 to about 0.5% of hyaluronic acid is used, and preferably these components are used in a weight ratio of 7:2:1, respectively.

In one embodiment of the invention, the polymeric matrix may be prepared according to the following state of the art derived procedure (Haifeng L. et al. 2004):

a gelatin solution (1% w/v) is mixed with a chitosan (2% w/v) solution, in 1% v/v acetic acid solution, together with a hyaluronic acid (0.01% w/v) solution. Said mixture is homogenized by stirring at 50° C., during 30 minutes, subsequently the mixture is poured in a container or device for shaping it, for example a Petri dish until the desired height. Subsequently, the plate containing the mixture is cooled at 4° C., until a gel is formed, which may subsequently be frozen at −20° C., during 8 hours, or at −80° C. during 6 hours. Said frozen gel is carefully immersed in liquid nitrogen, during 2 to 5 minutes, and finally is lyophilized during 24-48 hours.

Then, the lyophilized polymer is submerged in 20 mL of a 50 mM 2-morpholine-ethane sulfonic acid (MES) solution, 90% ethanol, during 30 minutes at room temperature. Subsequently, the cross-linking is achieved submerging the obtained matrix in 20 mL of a cross-linking solution which is composed by 50 mM MES, 30 mM 1-ethyl-(3,3-dimethyl-aminopropyl)carbodiimide (EDC) and 8 mM N-hydroxysuccinimide (NHS), in a 1:9 water:ethanol mixture. Then, the matrix is allowed to stand for about 2 hours, washed with ethanol, frozen and submerged in liquid nitrogen for about 2 to 5 minutes, finally lyophilizing the obtained cross-linked polymeric matrix.

Alternatively, the formed IIS is a biocompatible, cells-free, reticulated matrix, and which provides an easy to handle support, for a cells population to be integrated, previous to the implanting, comprising the components of a polymer or gel which is in situ polymerized. Wherein said matrix may comprise the above indicated components, and may be obtained according to the above disclosed embodiments.

In this embodiment of the invention, the cells used for being integrated within the matrix, embedded therein in order to form one embodiment of the SII, may be obtained from the patient to be treated (autologous), may be obtained from other human subject (allogenic), or may be obtained from other species (xenogenics), or obtained from many other sources (chimeric). In one preferred embodiment of the invention, the cells used in the development of the IIS are autologous skin cells, either from dermis and/or epidermis. Then, for developing the present invention, can be used epidermal cells, which may be selected, for example, from keratinocytes, melanocytes, immunocytes, stem cells or others; and/or dermal cells, selected, per example, from fibroblasts, endothelial cells, immunocytes, nervous cells, myocytes, stem cells or others.

The cells which will form the IIS may be grown as a pure culture or as a mixed culture. Once a suitable number of cells are obtained, the cellular populations are harvested for their inclusion within the matrix. In the embodiments of the invention, the cells may be integrated into the matrix, in solutions containing a concentration of up to $8 \times 10^6$, preferably between $2 \times 10^2$ to $4 \times 10^6$, more preferably between $3.5 \times 10^2$ to $4 \times 10^6$, and the most preferred about $1 \times 10^5$ cells/mL. In one embodiment of the invention, the used cells are dermal and/or epidermal cells, the ratio of the cells used for inoculating the matrix is comprised within the range of about 20:1 to 1:20 of dermal cells:epidermal cells, in a preferred manner in ratios from 1:1 to 1:10, more preferably between 1:2 and 1:5, considering the usual ratios as from 1:2 to 1:4.

In other preferred embodiment of the invention, the IIS is used as a temporary skin substitute. In this embodiment, the matrix may be seeded with cells having non autologous genotypes.

Further, the invention is intended as a method to prepare said IIS for surgical grafting on skin wounds. On a biocompatible and porous matrix, as those previously described, one of the gel components is deposited, therefore incorporating it easily and quickly into the matrix, after which the next component is added causing the in situ gel formation. Said gelified matrix is incubated under appropriate conditions for forming the IIS of the invention. In a preferred embodiment, on a biocompatible, porous matrix, as those described in the present invention, a desired cells suspension is deposited, contained in one of the gel component, in order to easily and quickly incorporate the cells into the matrix, after which the next component is added, causing the in situ gel formation.

Said inoculated and gelified matrix is incubated under proper conditions for obtaining the integrated implant system (IIS) of the invention.

In one preferred embodiment of the present invention, the IIS comprises dermal cells and/or epidermal cells population cultured under suitable conditions and which are obtained in the conventional manner, as described in the state of the art, which are deposited as a part of a cells suspension in a thrombin solution, onto the matrix. Then, the integration of said cellular suspension within the matrix is carried out, preferably through the use of a thrombin and fibrinogen system, in such a way that a fibrin polymer is produced in situ resulting in an gel like environment, which allows the cells to get embedded within the matrix.

Alternatively, in the present invention, other system could be used for generating a gel with adhesive properties, such as the combinations of cyanoacrylate esters/water or amine, gelatin-resorcinol/aldehyde, natural bioadhesives/enzymes. Once incubated this IIS, it is considered in condition or ready for being surgically grafted to the patient, which can be carried out during the first day, i.e. in a period no longer than 24 hours, in one embodiment of the invention, from the moment when the desired cells, available in a culture, are integrated into the matrix. The availability of cultured cells highly reduces the need of a skin donor, in order to complete the closing of the extended and full thickness skin wounds.

The cells suspension has a concentration of up to $8 \times 10^6$ cells/mL, preferably between $2 \times 10^2$ to $4 \times 10^6$, more preferably between $3.5 \times 10^2$ to $4 \times 10^6$, and in a preferred modality about $1 \times 10^5$, wherein the cells are suspended in a thrombin solution at a concentration comprised between 25 to 750 NIH/mL (NIH: Enzymatic Activity Units), more preferably 125 to 500 NIH/mL and in a preferred manner about 250 NIH/mL.

The described fibrinogen solution can be used at a concentration comprised between 10 to 90 mg/mL, preferably between 10-50 mg/mL, preferably 15-30 mg/mL and more preferably about 20 mg/mL.

In order to produce the IIS, between 50-500 µL, preferably between 50-250 µL and more preferably about 100 µL/cm$^2$ of a thrombin solution are applied into the matrix. Once the previous solution is absorbed, a fibrinogen solution at a ratio of 50 to 500 µL/cm$^2$, preferably between 50-250 µL/cm$^2$ and more preferably of about 100 µL/cm$^2$ is applied onto the matrix, producing the fibrin gel formation, which gets incorporated, i.e. it gets integrated, into the matrix, providing a IIS wherein matrix and gel are closely integrated in the matrix depth. The thrombin:fibrinogen ratio may fluctuate from 1:0.5 to 1:5, preferably 1:0.5 to 1:2.5 and in a more preferred ratio 1:1.

Figure 3:
FIG. 3. Correspond to microphotography of histological, longitudinal sections of an integrated implant. Wherein, photograph A corresponds to a layer of the IIS upper surface, observed with magnification (scale bar=100 μm) wherein is observed the more homogeneous fibrin matrix (blue) and the reticular polymer weave (red) and photograph B corresponds to a higher magnification of photograph A (scale bar=20 μm). Cells mainly located at the fibrin matrix are observed (arrows) and also in the reticular polymer weave (arrow tip). These microphotographs are notable as evidence of the closer integration among the system components: matrix-gel-cells. The above results support and clarify the components integration, which turns the present invention as different regarding the state of the art.

In one preferred embodiment for structuring the IIS, with the thrombin solution, suspended cells can be added in said solution, in such a way that when the fibrinogen is added, a fibrin gel is formed, wherein the gel gets integrated into the matrix and together to this the applied cells, such that in the IIS, the components are closely related, in the full depth of the matrix, the gel, the cells with the matrix, as can be appreciated in FIG. 3. Finally, the gel-matrix-cells IIS is submerged in a suitable media, which can be selected from DMEM/F-12, DMEM, RPMI or MEM, among others; preferably it is submerged in DMEM/F-12 culture media.

In one preferred modality, the IIS and the method of the invention exhibit a great contribution and advantage, since they incorporate both the main skin cellular populations, i.e. fibroblasts and keratinocytes. For an appropriate restoration of the injured or damaged skin area, said condition results ideal. In said preferred embodiment, both cells types are integrated, simultaneously, within the gel-matrix-cells IIS. Preferably, said cells are autologous and the keratinocytes are not differentiated, therefore, they have a great potential for proliferation.

Other advantageous factor of the IIS of one of the embodiments of the invention, as it has been mentioned, is that the cells are included, i.e. embedded within the IIS. The IIS performs as a carrier system, adapts to the shape of the wound, with an appropriate adjustment, which does not require of methods, devices or additional adhesives for fixing the IIS to the skin wound to be treated. Furthermore, it is 100% biodegradable, having been identified the in vitro ability of the cells integrated into the IIS of moving to the IIS surroundings (data not shown). The carrier components are non-inert and exhibit antibacterial, chemotactic and proangiogenic properties, helping to an earlier wound healing. From a handling point of view, the IIS does not require of additional supports neither of adhesives, which is highly beneficial since with a single and direct application the graft "starting" can be achieved, i.e. it gets adhered almost immediately, without the need of additional components or products for adhering it.

Once the integrated implant system has been grafted to the patient, and once the biodegradable matrix has been reabsorbed by the body, the cells get organized in order to form a functional skin tissue. The device comprises many of the properties and structures that are found in the normal non-damaged skin, and functions as in the usual way as does a non damaged skin, in order to protect the subject from the fluids loss and against bacterial infections. The integrated implant system establishes a basement membrane, and maintains the same anatomical configuration for the layers or cell populations in the same way as usually occurs in the non-damaged skin.

The following examples and the detailed description of the invention, are related to the most preferred embodiments for carrying out the invention, however, these are not intended to restrict the scope of the invention.

EXAMPLE 1

Construction of the Integrated Implant System (IIS)

For manufacturing the IIS the following solutions must be prepared:

a) Calcium Chloride and Sodium Chloride Solution.

About 3 to 12 g of di-hydrate calcium chloride are dissolved in 1 liter of sterile milli-Q water (Millipore). Sodium chloride is added until a solution with an osmolarity comprised between 280-320 mOsm/L, is obtained. Preferably 4.5 g of di-hydrate CaCl2 and 6.1 g of NaCl in 1 liter of water (300 mOsm/L), are used.

b) Fibrinogen Solution

An amount between 10 and 90 mg of fibrinogen in 1 mL of sterile Milli-Q water, is dissolved. Preferably, 20 mg of a lyophilized product is used, with a minimal concentration of 65% (13 mg).

c) Thrombin Solution

In 1 mL of sterile calcium chloride and sodium chloride solution, between 250 and 500 NIH thrombin are dissolved. Preferably, 1 mg of a lyophilized product with an activity of 258 NIH/mg-lyophilized product (258 NIH) is used.

d) Integrated Implant System Preparation

The IIS preparation is always carried out in a sterile environment. Thus, a polymeric matrix portion is provided, which is either commercially available or prepared according to the above indicated process, in an appropriate size for the required application. The matrix portion is sterilized, through methods usually known in the state of the art, as for instance, through irradiation, UV treatment or with and alcohol solution, without being restricted to said options. In one preferred embodiment, the matrix portion is submerged for a suitable time period, preferably for about 1 hour, in an aqueous alcohol solution, wherein said alcohol corresponds to a 50% to 90% alcohol solution in sterile Milli-Q water, preferably a 70% aqueous alcohol solution, wherein the alcohol is selected from the group consisting of ethanol, propanol and iso-propanol. Then, the matrix is removed and dried over a sterile absorbent paper. The matrix is placed in a suitable sterile container (for example, a Petri dish or other sterile container with appropriate dimensions for the selected matrix portion) and over the matrix portion a thrombin solution is spread at a ratio of about 100 µL solution, to be applied over about 1 cm$^2$ of the polymer. Subsequently, the absorption of the solution is allowed, which usually takes place within the first three minutes, preferable before 2 minutes. Then, about 100 µL/cm$^2$ of fibrinogen is added over the matrix containing the absorbed solution. Subsequently, the clot formation is visually verified, which means that the IIS can be immediately used or conserved for later applications.

EXAMPLE 2

Construction of the Integrated Implant System (IIS) Containing Cells

In a complementary manner to the description of example 1, in one preferred embodiment of the invention, it is possible to prepare an IIS containing the desired cells integrated into the matrix-gel system. For such a case, the matrix is prepared as described above and additionally a cellular suspension is prepared, for which the cells from a cell culture obtained through trypsinization, are centrifuged in order to obtain a pellet, which is suspended in 1 mL of a CaCl$_2$ and NaCl-containing thrombin solution.

The IIS preparation is always carried out in a sterile environment. Therefore, a polymeric matrix portion is provided, which can be either commercially available or prepared according to the above-indicated process, in an appropriate size. The matrix is submerged during a suitable time period, preferably for about 1 hour, in an aqueous alcohol solution, wherein said alcohol corresponds to a 50% to 90% alcohol solution in sterile Milli-Q water, preferably it corresponds to an aqueous 70% alcohol solution, wherein the alcohol is selected from the group consisting of ethanol, propanol and iso-propanol. Then, the matrix is removed and dried over sterile absorbent paper. Subsequently, the dried matrix is submerged in DMEM/F12 (10% FBS) media, for about 18 to 30 hours, preferably during less or about 24 hours. The sterility is checked through microscopy observation, by the media turbidity and the appearance of change in color. Subsequently, the polymer is removed, and once more dried over sterile absorbent paper.

The matrix is placed in a suitable sterile container, for example, a Petri dish or other sterile container with appropriate dimensions for the selected matrix portion. Over said matrix portion, 100 µL of a thrombin and cells solution are spread, containing a maximum of up to $8 \times 10^6$, preferably between $2 \times 10^2$ to $4 \times 10^6$, more preferably between $3.5 \times 10^2$ and $3.5 \times 10^6$ cells/mL of final solution, preferably a suspension containing about $2 \times 10^5$ cells/mL of solution, for being applied onto about 1 cm$^2$ of the matrix. Then, the absorption of the cellular suspension is allowed, which generally occurs within the first three minutes, preferably before 2 minutes. Subsequently, over the matrix containing the absorbed suspension, 100 µL/cm$^2$ of fibrinogen are added. Later, the clot formation is visually verified, and the obtained implant system is submerged in DMEM/F-12 (10% FBS) culture media.

Wherein, the cells suspension corresponds to allogenic cells, autologous cells or stem cells, wherein the cells come from a cellular culture for each of said cellular types, and which have been isolated from biopsies obtained according to standard procedures described in the state of the art. In one embodiment of the present invention, said cellular cultures correspond to an autologous fibroblasts cellular culture, or to an autologous keratinocytes cellular culture, or to a stem cell culture, or a mixture thereof, in a calcium chloride (30 mM) and sodium chloride (100 mM) solution. In a preferred embodiment of the present invention, the cells suspension contains an autologous fibroblasts and autologous keratinocytes combination.

EXAMPLE 3

Figure 4:
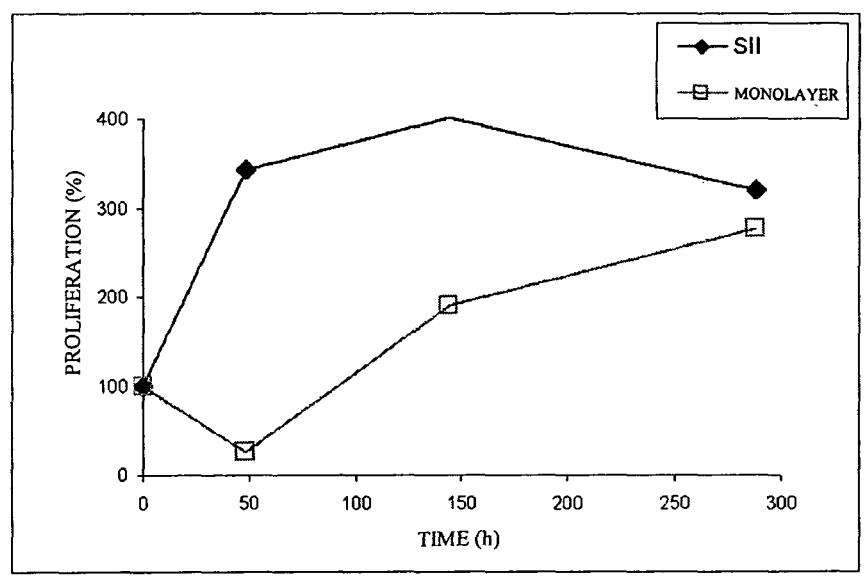
FIG. 4. Presents a plot showing the kinetics of cellular proliferation in an integrated implant system (IIS) like the one of the present invention and the proliferation in a monolayer system within a culture flask, for fibroblasts, at $4 \times 10^4$ cell/$cm^2$, as the initial concentration. The high proliferation, up to 300% in the first 48 hours, turns this development in an effective tool at 24 hours, wherein the growth is of 200%, an advantageous situation for the treatment of critical patients.

Growth Characteristics of the Cells Incorporated into the IIS (FIG. 4)

The ability of growing of those cells incorporated into an SII, prepared according to example 2, was evaluated. The existence of a time, wherein cells are in their maximum proliferative ability, was determined.

Comparing the growth behaviour on a monolayer system, as it takes place in the state of the art devices, wherein the cells grow on the polymers surface or on mechanical supports, in regard to the ISS of the present invention, it was found that the IIS shows clear and outstanding advantages, which could result in better healing and recovery ability of those patients treated with the device of the present invention.

The cell cultures in the IIS show that during the first 50 hours of culture, an outstanding increase of the proliferation is achieved, in regard to the monolayer system (FIG. 4). The latter is a relevant advantage of the present invention, insofar as 24 hours from the assembly and seeding of the IIS, it is possible to proceed to implanting it onto the cutaneous lesions, wherein the IIS comprises cells in an increasing and active curve of a maximum proliferation ability, which may provide better qualities and lower recovery time in the lesion to which the IIS is applied.

EXAMPLE 4

Preclinical IIS Application on Rabbits

Rabbits were surgically prepared, in order to receive the IIS, this corresponds to the extraction of circular zones 2.5 cm in diameter of dermis and epidermis from the animal's dorsal area.

Those animals that were not treated showed a critical clinical condition, resulting in 33% of deaths. On the contrary, those rabbits that were immediately treated with different IIS, survived the trial in excellent conditions (n=8).

The dorsal section of the animal being curve, makes it difficult to maintain implant devices on place. However, the application of the IIS did not show those difficulties, being expedite, of easy handling and adhesion in different zones of the assayed animal. On the other hand, when a fibrin gel with cells was applied, as occurs in some state of the art devices, it resulted complicated in handling, difficult to maintain on place in the lesion and with poor adhesion.

The animals treated with the IIS, showed very low infections incidence and when these occurred, they shared the feature of spontaneously disappearing. This may mean that the IIS rapidly reconstitutes the functional skin systems that provide recovery qualities to the damaged area.

No clinical evidences of rejection against any of the components of the graft were observed during the trials. Additionally, are epithelization in the damaged area was noticed, within a 25 days period, which was confirmed through a clinical and histological evaluation.

The set of examples and the invention description, without the intention of restricting, provide evidences about the differences and advantages of the present invention regarding the currently known and disclosed devices, which are powerful and enough qualities, in the sight of any person skilled in the art, which further allow differentiating the present invention of the matter known in the state of the art, and certainly, cannot be deduced or obviously derived from said background.

REFERENCES

1. Michel M, L'Heureux N L, Auger F A, Germain L. From newborn to adult: Phenotypic and functional properties of skin equivalent and human skin as a function of donor age. J Cell Physiol 1997; 171:179-81.
2. Bello Y M, Falabella A F, Eaglstein W H. Tissue-engineered skin: Current status in wound healing. Am J Clin Dermatol 2001; 2:305-13.
3. Eisenbud, D, Huang N F, Luke, S. Silberklang, M. Wounds 2004; 16(1):2-17.
4. Carsin H, Ainaud P, Le Bever H, et al. Cultured epithelial autografts in extensive burn coverage of severely traumatized patients: A five year single-center experience with 30 patients. Burns 2000; 26:379-87.
5. Lam P K, Chan E S Y, To E W H, et al. Development and evaluation of a new composite Laserskin graft. J Trauma 1999; 47:918.
6. Khachemoune A, Bello Y M, Phillips T J. Factors that influence healing in chronic venous ulcers treated with cryopreserved human epidermal cultures. Dermatol Surg 2002; 28:274-80.
7. Alvarez-Diaz C, Cuenca-Pardo J, Sosa-Serrano A, et al. Burns treated with frozen cultured human allogeneic epidermal sheets. J Burn Care Rehabil 2000; 21:291-9.
8. Naughton G, Mansbridge J, Gentzkow G. A metabolically active human dermal replacement for the treatment of diabetic foot ulcers. Artificial Organs 1997; 21:1203-10.
9. Pollack R, Edington H, Jensen J, et al. A human dermal replacement for the treatment of diabetic foot ulcers. WOUNDS 1997; 9:175-83.
10. Hansbrough J F, Mozingo D W, Kealey G P, et al. Clinical trials of a biosynthetic temporary skin replacement, Dermagraft-Transitional Covering, compared with cryopreserved human cadaver skin for temporary coverage of excised burn wounds. J Burn Care Rehabil 1997; 18:43-51.
11. Curran M P, Plosker G L. Bilayered bioengineered skin substitute (Apligraf): A review of its use in the treatment of venous leg ulcers and diabetic foot ulcers. Bio Drugs 2002; 16:439-55.
12. Maas-Szabowski N, Stark H-J, Fusenig N E. Keratinocyte growth regulation in defined organotypic cultures through Il-1 induced KGF expression in resting fibroblasts. J Invest Dermatol 2000; 14:1075-84.
13. Stark H-J, Maas-Szabowski H, Smola H, et al. Organotypic keratinocyte-fibroblast co-cultures: In vitro skin equivalents to study the molecular mechanisms of cutaneous regeneration. In: Horch R E, Munster A M, Achauer B M (eds). Cultured Human Keratinocytes and Tissue Engineered Skin Substitutes. Stuttgart, Germany: Georg Thieme Verlag, 2001.
14. Betterman A., Kage A., Salomon A., Schneider C., Hubner H., Buchholz R., (1999), Cultivation of human skin cells in fibrin microcapsules, Second International Congress Current Concepts in Pediatric Burn Care.

The invention claimed is:

1. A method for preparing an implant system that comprises a sterile, porous, biocompatible polymeric matrix and a gel intimately associated in the interior of the matrix, wherein the method is carried out in a sterile environment and comprises the steps of:
   a) providing a tridimensional polymeric matrix structure that comprises crosslinked gelatine, chitosan and hyaluronic acid;
   b) next, applying to said tridimensional polymeric matrix structure a volume of a solution comprising thrombin and cells;
   c) allowing the solution to be absorbed in the tridimensional polymeric matrix structure, during an appropriate time of period;
   d) then adding a fibrinogen solution to form a gel that is integrated in situ to the tridimensional polymeric matrix structure; and
   e) incubating the gel-integrated tridimensional polymeric matrix structure under conditions appropriate for forming an implant system.

2. The method for preparing an implant system, according to claim 1, wherein prior to step b) the tridimensional polymeric matrix structure of step a) is immersed in an alcoholic solution, during one hour; removed from the alcoholic solution and dried; and subsequently submerged in Dulbecco's Modified Eagle's Medium and Ham's F-12 Nutrient Mixture (DMEM/F12) medium during a time period of about 18 hours to about 30 hours.

3. The method for preparing the implant system, according to the claim 1, wherein the sterile environment is achieved through irradiation or ultraviolet (UV) light.

4. The method for preparing an implant system, according to claim 2, wherein the method further comprises submerging the formed implant system in DMEM/F-12, DMEM, Roswell Park Memorial Institute (RPMI) or Minimum Essential Media (MEM) medium.

5. The method for preparing an implant system, according to claim 2, wherein the alcoholic solution consists of a solution comprising sterile water and an alcohol selected from the group consisting of ethanol, propanol or isopropanol, and mixtures thereof.

6. The method according to claim 1 wherein the method is carried out ex vivo in a sterile environment, wherein the solution consists of thrombin and cells, the step of allowing the solution to be absorbed during the appropriate time of period to absorb the cells and the thrombin throughout the matrix structure, and the gel formed with the thrombin is integrated with the cells within the interior of the tridimensional polymeric matrix structure.

7. The method according to claim 1 wherein the cells and thrombin of step c) are absorbed through the full depth or thickness of the matrix.

* * * * *